US012667566B2

(12) United States Patent
Patil et al.

(10) Patent No.: US 12,667,566 B2
(45) Date of Patent: Jun. 30, 2026

(54) COMBINATION THERAPY OF GPR119 AGONISTS AND DPP-4 INHIBITORS

(71) Applicant: MANKIND PHARMA LTD., New Delhi (IN)

(72) Inventors: Rakesh Iswar Patil, Manesar (IN); Sazid Ali, Manesar (IN); Srinivasa Reddy Bapuram, Manesar (IN); Santosh Kumar Rai, Manesar (IN); Anil Kumar, Manesar (IN)

(73) Assignee: MANKIND PHARMA LTD., New Delhi (IN)

(*) Notice: Subject to any disclaimer, the term of this patent is extended or adjusted under 35 U.S.C. 154(b) by 1061 days.

(21) Appl. No.: 17/625,429

(22) PCT Filed: Jun. 23, 2020

(86) PCT No.: PCT/IB2020/055911

§ 371 (c)(1),
(2) Date: Jan. 7, 2022

(87) PCT Pub. No.: WO2021/005436

PCT Pub. Date: Jan. 14, 2021

(65) Prior Publication Data

US 2022/0265652 A1 Aug. 25, 2022

(30) Foreign Application Priority Data

Jul. 8, 2019 (IN) ............................. 201911027191

(51) Int. Cl.

| | |
|---|---|
| ***A61K 31/506*** | (2006.01) |
| ***A61K 9/20*** | (2006.01) |
| ***A61K 31/40*** | (2006.01) |
| ***A61K 31/403*** | (2006.01) |
| ***A61K 31/4162*** | (2006.01) |
| ***A61K 31/454*** | (2006.01) |
| ***A61K 31/4545*** | (2006.01) |
| ***A61K 31/4745*** | (2006.01) |
| ***A61K 31/495*** | (2006.01) |
| ***A61K 31/4985*** | (2006.01) |
| ***A61K 31/513*** | (2006.01) |
| ***A61K 31/519*** | (2006.01) |
| ***A61K 31/522*** | (2006.01) |
| ***A61K 31/69*** | (2006.01) |
| ***A61P 3/10*** | (2006.01) |

(52) U.S. Cl.
CPC .......... *A61K 31/506* (2013.01); *A61K 9/2018* (2013.01); *A61K 9/2059* (2013.01); *A61K 31/40* (2013.01); *A61K 31/403* (2013.01); *A61K 31/4162* (2013.01); *A61K 31/454* (2013.01); *A61K 31/4545* (2013.01); *A61K 31/4745* (2013.01); *A61K 31/495* (2013.01); *A61K 31/4985* (2013.01); *A61K 31/513* (2013.01); *A61K 31/519* (2013.01); *A61K 31/522* (2013.01); *A61K 31/69* (2013.01); *A61P 3/10* (2018.01)

(58) Field of Classification Search
CPC .................................................... A61K 31/506
See application file for complete search history.

(56) References Cited

U.S. PATENT DOCUMENTS

| | | | | |
|---|---|---|---|---|
| 10,208,030 B2 | 2/2019 | Patil et al. | | |
| 2009/0247532 A1* | 10/2009 | Huang | ................ | C07D 487/04 514/249 |
| 2017/0291894 A1* | 10/2017 | Patil | ......................... | A61P 3/00 |

FOREIGN PATENT DOCUMENTS

| | | |
|---|---|---|
| WO | 2006/076231 | 7/2006 |
| WO | 2007/120702 | 10/2007 |
| WO | 2009/123992 | 10/2009 |
| WO | 2010/029089 | 3/2010 |
| WO | 2011/113947 | 9/2011 |
| WO | 2017/175066 | 10/2017 |

OTHER PUBLICATIONS

International Search Report and Written Opinion, issued in the corresponding PCT application No. PCT/IB2020/055911, dated Sep. 29, 2020, 10 pages.

Soga et al., "Lysophosphatidylcholine enhances glucose-dependent insulin secretion via an orphan G-protein-coupled receptor", Biochemical and Biophysical Research Communications, vol. 326, 2005, pp. 744-751.

* cited by examiner

*Primary Examiner* — Yong S. Chong
(74) *Attorney, Agent, or Firm* — HSML P.C.

(57) ABSTRACT

The present invention relates to combinations of GPR119 receptor agonists with DPP-4 inhibitors and their use thereof for treating or preventing cardiovascular and metabolic disorders, including diabetes mellitus, non-alcoholic fatty liver disease (NAFLD), NAFL, NASH, dyslipidemia, and related disorders thereto.

7 Claims, 2 Drawing Sheets

*Significant difference as compared to Vehicle Group. #Significant difference as compared to compound of Formula Ia (10 mg/kg, P.O.). *P < 0.05, P < 0.01 & *P < 0.001, #P < 0.05

*Significant difference as compared to Vehicle Group. #Significant difference as compared to compound of Formula Ia (10 mg/kg, P.O.), *P < 0.05, $$$/***/###P < 0.001

COMBINATION THERAPY OF GPR119 AGONISTS AND DPP-4 INHIBITORS

FIELD OF THE INVENTION

The present invention relates to the combinations of GPR119 agonists with DPP-4 inhibitors, as well as to the use of these combinations for treating and/or preventing cardiovascular and metabolic disorders, including diabetes mellitus, non-alcoholic fatty liver disease (NAFLD), NAFL, NASH, dyslipidemia, and related disorders thereto.

BACKGROUND OF THE INVENTION

Diabetes is a life-style related disease derived from multiple causative factors. It is characterized by elevated levels of plasma glucose (hyperglycemia) in the fasting state or after administration of glucose during an oral glucose tolerance test. There are two generally recognized forms of diabetes: type 1 and type 2 diabetes mellitus. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

Diabetes is one of the leading cause of damage to the retina at the back of the eye and increases risk of cataracts and glaucoma. It is also associated with nerve damage, especially in the legs and feet, which interferes with the ability to sense pain and contributes to serious infections. Diabetes has also been implicated in the development of kidney disease, eye diseases and nervous-system problems. Taken together, diabetes complications are one of leading causes of death worldwide.

Obesity is the result of an imbalance between caloric intake and energy expenditure. It is highly correlated with insulin resistance and diabetes. However, the molecular mechanisms that are involved in obesity-diabetes syndromes are not clear.

During early development of obesity, increased insulin secretion balances insulin resistance and protects patients from hyperglycemia, but after several decades, [beta] cell function deteriorates and non-insulin-dependent diabetes develops in about 20% of the obese population. Obesity has thus become the leading risk factor for diabetes, however, the factors which predispose a fraction of patients to alteration of insulin secretion in response to fat accumulation remain currently unknown. Obesity considerably increases the risk of developing cardiovascular diseases as well.

Non-alcoholic fatty liver disease (NAFLD), comprising several liver diseases including NAFL and NASH, which is the most frequent liver disease world-wide, is a clinical manifestation of overweight and metabolic syndrome such as T2DM.

The treatment of T2DM generally begins weight loss, healthy diet and exercise program. Although these factors are important especially to dissolve the increased risk of cardiovascular disorders related to diabetes mellitus, they are not effective generally for the control of diabetes mellitus itself. There are many drugs useful for the treatment of diabetes mellitus, including insulin, metformin, sulfonylureas, acarbose, thiazolidinedione, GLP-1 analogue and DPP-4 inhibitors. There are, however deficiencies associated with currently available treatment, including hypoglycemic episodes, weight gain, loss in responsiveness to therapy over time, gastrointestinal problems, and edema. Therefore, there is an unmet medical need for pharmaceutical combinations with a good efficacy with regard to glycemic control, with regard to disease-modifying properties and with regard to reduction of cardiovascular morbidity and mortality while at the same time showing an improved safety profile.

Although a number of receptor classes exist in humans, by far the most abundant and therapeutically relevant is represented by the G protein-coupled receptor (GPCR) class, it is estimated that approximately 4% of the protein-coding genome encodes GPCRs. GPCRs are also known as seven-transmembrane domain receptors as they share a common structural motif, having seven sequences of between 22 to 24 hydrophobic amino acids that form seven alpha helices, each of which spans the membrane. Further, there has been renewed focus on pancreatic islet-based insulin secretion that is controlled by glucose-dependent insulin secretion (GDIS). In this regard, several orphan G-protein coupled receptors (GPCR's) have recently been identified that are preferentially expressed in the beta-cell and are implicated in GDIS.

GPR119 is a cell-surface GPCR that is highly expressed in human (and rodent) islets as well as in insulin-secreting cell lines. Activation of GPR119 has been demonstrated to stimulate intracellular cAMP and lead to glucose dependent GLP-1 and insulin secretion (T. Soga et al Biochem. Biophys. Res. Commun. 2005, 326). Synthetic GPR119 agonists augment the release of insulin from isolated static mouse islets only under conditions of elevated glucose, and improve glucose tolerance in diabetic mice and diet-induced obese (DIO) C57/B6 mice without causing hypoglycemia.

Further, the enzyme DPP-4 (dipeptidyl peptidase IV) also known as CD26 is a serine protease known to lead to the cleavage of a dipeptide from the N-terminal end of a number of proteins having at their N-terminal end a proline or alanine residue. Due to this property DPP-4 inhibitors interfere with the plasma level of bioactive peptides including the peptide GLP-1 and are considered to be promising drugs for the treatment of diabetes mellitus.

U.S. Pat. No. 10,208,030 B2 discloses novel compounds which act as GPR119 receptor agonists which is incorporated herein by reference in its entirety.

PCT publication Nos. WO 2006/076231, WO 2007/120702, WO 2010/029089, WO 2011/113947, WO 2010/029089 and WO 2011/113947 disclose the pharmaceutical combination which are useful in the treatment and prevention of metabolic disorders, including diabetes mellitus (type I and type II), and related disorders.

Although various combinations are known from prior known references, there still remains a need for pharmaceutical combinations using GPR119 agonists along with DPP-4 inhibitors to treat or prevent cardiovascular and metabolic disorders. The combination of a GPR119 agonist of Formula I and DPP-4 inhibitors, has surprising and particularly advantageous properties, which make these combinations particularly suitable for treating and preventing cardiovascular diseases and metabolic disorders, including diabetes mellitus, and conditions related thereto.

OBJECTIVE OF THE INVENTION

The objective of the present invention is to provide combinations of GPR119 agonists and DPP-4 inhibitors, as well as to the use of these combinations for treating and preventing cardiovascular and metabolic disorders, including diabetes mellitus; non-alcoholic fatty liver disease (NAFLD), comprising several liver diseases including NAFL and NASH; dyslipidemia and conditions related thereto.

SUMMARY OF THE INVENTION

In one aspect, the present invention provides pharmaceutical combination of GPR119 agonists and DPP-4 inhibitors, slowing progression of delaying or treating a metabolic disorder, in particular in improving glycemic control in patients. This opens up new therapeutic possibilities in the treatment and prevention of type 2 diabetes mellitus, overweight, obesity, complications of diabetes mellitus and of neighbouring disease states such as NAFLD and NASH.

In another aspect, the present invention provides a combination of therapeutic effective amount of GPR119 agonists of Formula I, tautomer, stereoisomer, pharmaceutically acceptable salt thereof, and a therapeutic effective amount of DPP-4 inhibitor or its pharmaceutically acceptable salt.

The term "therapeutically effective amount" as used herein means an amount of the GPR119 agonists of Formula I or that of DPP-4 inhibitors effective in producing the desired therapeutic response in a particular patient (subject) suffering from Type 2 diabetes mellitus, non-alcoholic fatty liver disease (NAFLD), NAFL, NASH, dyslipidemia, and related disorders. Particularly, the term "therapeutically effective amount" includes the amount of the therapeutic agents, which when administered will achieve the desired therapeutic effects. In the context of the present invention the desired therapeutic effects includes partial or total inhibition, delay or prevention of the progression of metabolic disorder, in particular in improving glycemic control in patients. In respect of the therapeutic amount of the therapeutic agents i.e. the GPR119 agonists of Formula I or that of DPP-4 inhibitors, consideration is also given that the amount of each of the therapeutic agent used, for the treatment of a subject is low enough to avoid undesired or severe side effects. The therapeutically effective amount of each of the GPR119 agonists of Formula I and DPP-4 inhibitors when used in combination will vary with the age and physical condition of the end user, the severity of disease, the duration of the treatment, the nature of any other concurrent therapy, the specific type of therapeutic agent employed for the treatment, the particular pharmaceutically acceptable carrier utilized in the pharmaceutical compositions containing the therapeutic agents.

Accordingly, in another aspect, the present invention provides a pharmaceutical combination comprising GPR119 agonists of Formula I, tautomer, stereoisomer, or pharmaceutically acceptable salt thereof and DPP-4 inhibitor or its pharmaceutically acceptable salt, wherein compound of Formula I is represented as:

Formula I

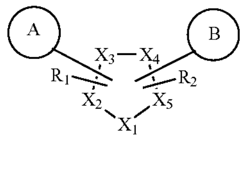

wherein, $X_1$, $X_2$, $X_3$, $X_4$ and $X_5$ are each independently N, O, S or CH; and $X_4$ and $X_5$ may optionally combine to form a five membered ring comprising one or more of heteroatoms each independently selected from N, O and S and the additional five membered ring may be further optionally substituted with one or more of group selected from F, Cl, Br, I, $CF_3$ and $C_{1-6}$ alkyl;

$R_1$ and $R_2$ is independently selected from the group comprising —H, —O, $C_{1-6}$ alkyl, $C_{1-6}$alkoxy, —$(CH_2)$n, amino, —CO, —CONH, —NH(Alkyl), —N(Alkyl)$_2$, —NH-aralkyl, —$CH_2O$, —$OCH(CH_3)_2$, halogenCOOR$_3$, —CONR$_3$R$_4$, NR$_3$COR$_4$;

$R_3$ and $R_4$ is independently selected from the group comprising hydrogen, or $C_{1-6}$ straight chain or branched chain alkyl which may be further substituted with halogen or $C_{1-6}$ alkyl;

n is 0, 1, 2 or 3.

A is selected from

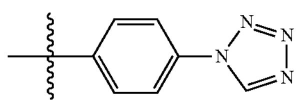

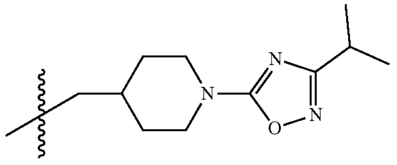

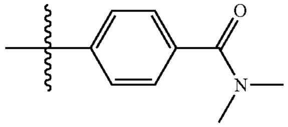

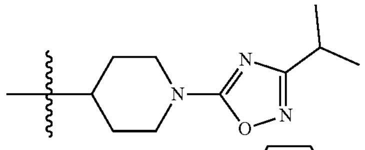

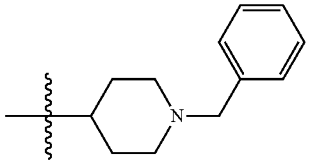

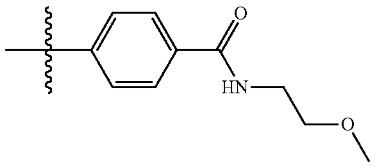

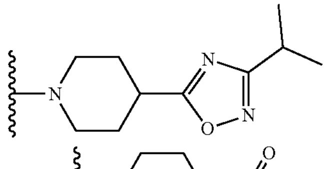

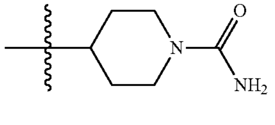

-continued
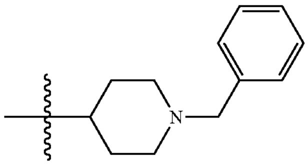
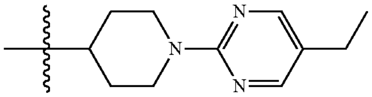
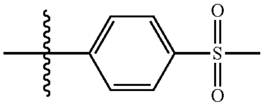
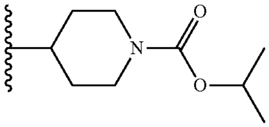
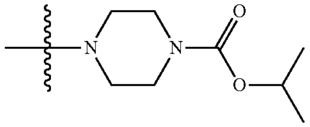
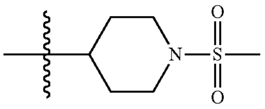
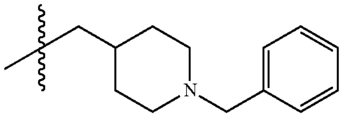
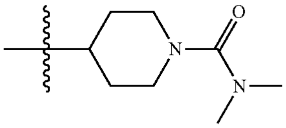
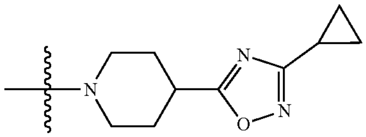
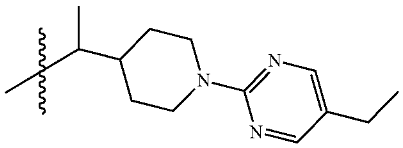
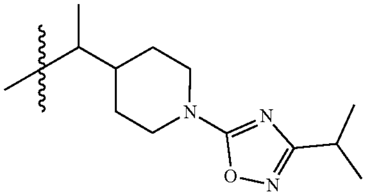
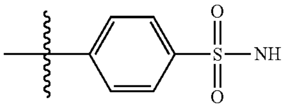
-continued
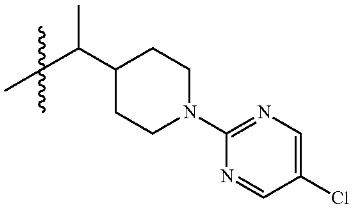
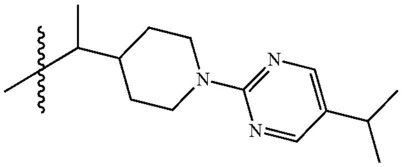
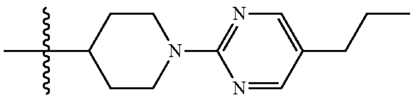
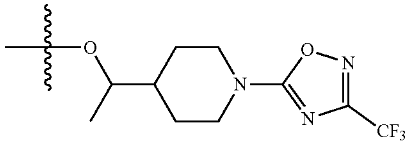
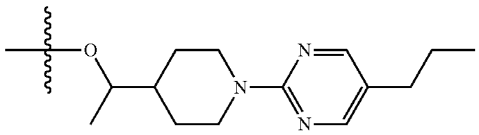
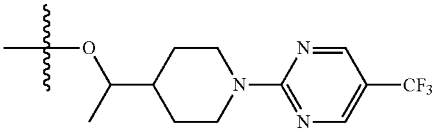
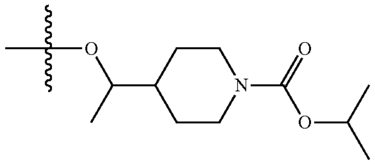
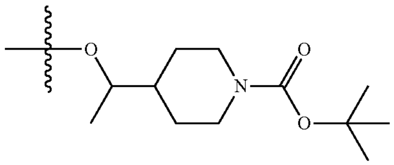
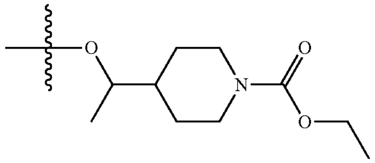
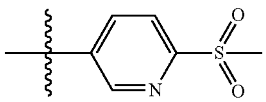
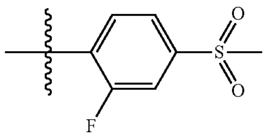

-continued
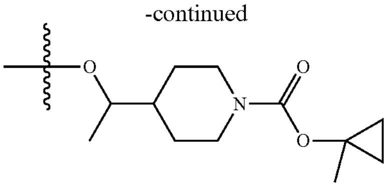
Ring B is be selected from
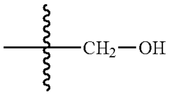
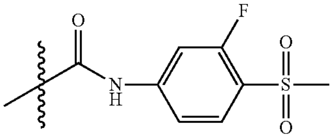
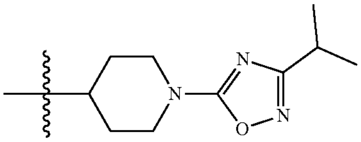
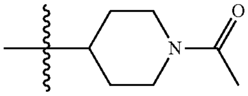
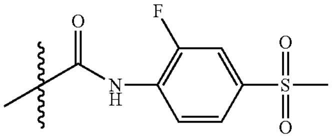
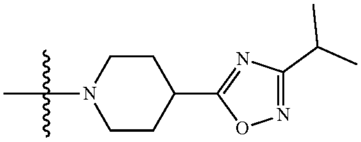
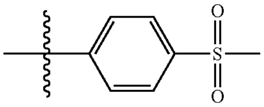
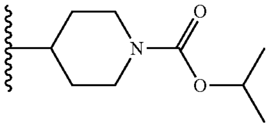
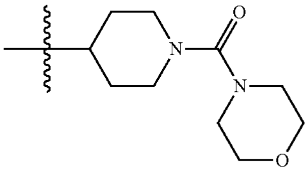
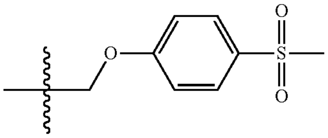
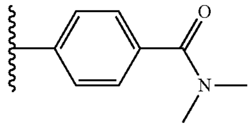
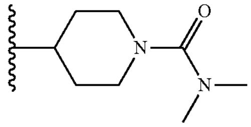
-continued
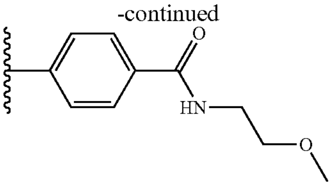
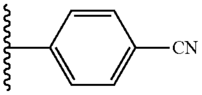
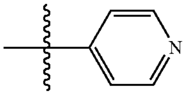
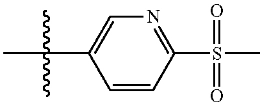
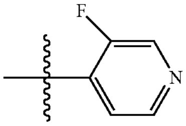
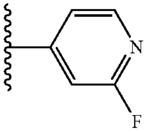
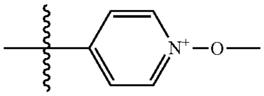
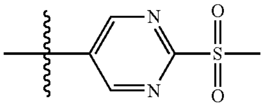
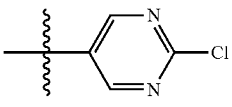
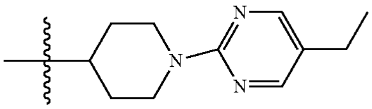
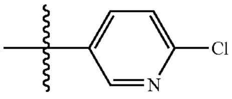
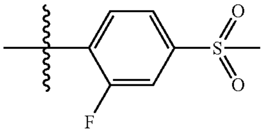
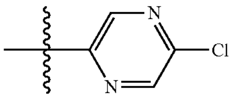
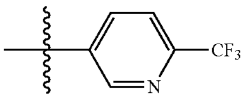
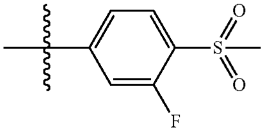
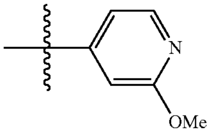
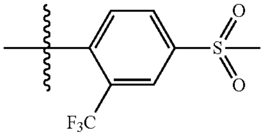
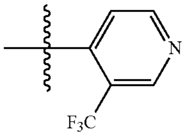
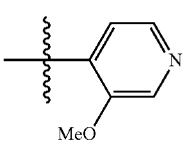
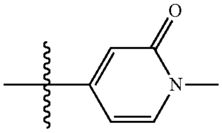
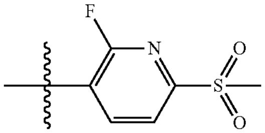
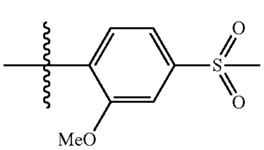
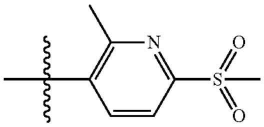
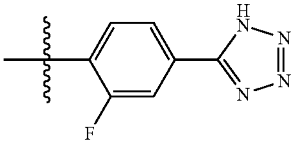

-continued

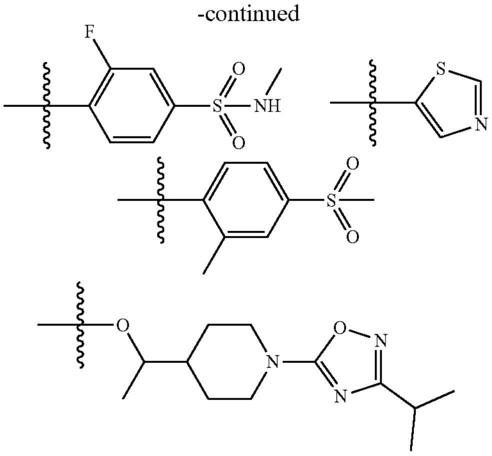

In another aspect, the present invention provides a pharmaceutical combination comprising GPR119 agonists of Formula I, tautomer, stereoisomer, or pharmaceutically acceptable salt thereof and DPP-4 inhibitor or its pharmaceutically acceptable salt, wherein said DPP-4 inhibitor is selected from the group comprising sitagliptin, vildagliptin, saxagliptin, linagliptin, carmegliptin, gosogliptin, alogliptin, melogliptin, gemigliptin, anagliptin, teneligliptin, trelagliptin, dutogliptin, evogliptin and omarigliptin.

In another aspect, the present invention provides a method for treating diabetes mellitus and related disorders by administering comprising GPR119 agonists of Formula I, tautomer, stereoisomer, or pharmaceutically acceptable salt thereof and DPP-4 inhibitor or its pharmaceutically acceptable salt, wherein GPR119 agonist and DPP-4 inhibitor are either administered simultaneously, concurrently, alternately or sequentially.

In another aspect, the present invention provides a method for treating non-alcoholic fatty liver disease (NAFLD), NAFL, NASH, dyslipidemia, and related disorders by administering comprising GPR119 agonists of Formula I, tautomer, stereoisomer, or pharmaceutically acceptable salt thereof and DPP-4 inhibitor or its pharmaceutically acceptable salt, wherein GPR119 agonist and DPP-4 inhibitor are either administered simultaneously, concurrently, alternately or sequentially.

In another aspect, the present invention provides a pharmaceutical combination comprising GPR119 agonists of Formula I tautomer, stereoisomer, or pharmaceutically acceptable salt thereof and DPP-4 inhibitor or its pharmaceutically acceptable salt, wherein the GPR119 agonist and DPP-4 inhibitor are present in a single dosage form or in separate dosage forms.

In another aspect, the present invention provides a pharmaceutical combination comprising GPR119 in an amount of about 0.001 mg to about 5000 mg and of DPP-4 inhibitor in an amount of about 1 mg to about 500 mg.

BRIEF DESCRIPTION OF THE DRAWINGS

The present disclosure will now be described with the help of the accompanying drawings, in which.

DETAILED DESCRIPTION OF THE INVENTION

Figure 1:
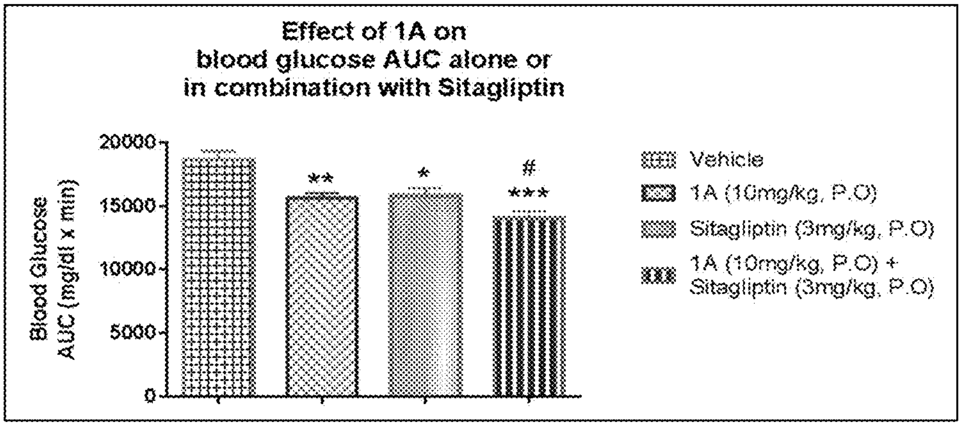
FIG. 1. Oral glucose tolerance test (OGTT) of GPR119 agonist Formula 1A in male Sprague Dawley rats. Formula 1A was administered to the rats and blood glucose was monitored post 30 min of dose administration (0-time point). After glucose administration (2 g/kg/10 ml), glucose levels were estimated at different time points (5, 15, 30, 60 & 120 min) and compared to vehicle group. Data was analysed by One-Way ANOVA followed by Dunnett's Multiple Comparison Test. *P<0.05, P<0.01 & *P<0.001 vs vehicle control. Vehicle used was 0.5% Tween 80 and 99.5% NaCMC in water (0.5% w/v).

The terms "pharmaceutically acceptable salt" or "salt" are used interchangeably in the context of the present invention. "Pharmaceutically acceptable salts" or "salts" as used in the context of the present invention refers to inorganic acids such as hydrochloric acid, hydrobromic acid, sulphuric acid, phosphoric acid salt, carbonate salts; organic acids such as succinic acid, formic acids, acetic acid, diphenyl acetic acid, palmoic acid, triphenylacetic acid, caprylic acid, dichloroacetic acid, trifluoro acetic acid, propionic acid, butyric acid, lactic acid, citric acid, gluconic acid, mandelic acid, tartaric acid, malic acid, adipic acid, aspartic acid, fumaric acid, glutamic acid, maleic acid, malonic acid, benzoic acid, p-chlorobenzoic acid, dibenzoyl tartaric acid, oxalic acid, nicotinic acid, o-hydroxybenzoic acid, p-hydroxybenzoic acid, 1-hydroxy-naphthalene-2-carboxylic acid, hydroxynaphthalene-2-carboxylic acid, ethanesulfonic acid, ethane-1,2-disulfonic acid, 2-hydroxyethane sulfonic acid, methanesulfonic acid, (+)-camphor-10-sulfonic acid, benzenesulfonic acid, naphthalene-2-sulfonic acid, p-toluenesulfonic acid and the like. The term "salt(s)", as employed herein, denotes inorganic and/or organic acids, particularly, pharmaceutically acceptable (i.e., non-toxic, physiologically acceptable) salts are preferred.

The present invention relates to combinations of GPR119 agonists and DPP-4 inhibitors, as well as to the use of these combinations for treating and preventing cardiovascular and metabolic disorders, including diabetes mellitus, non-alcoholic fatty liver disease (NAFLD), NAFL, NASH, dyslipidemia, and conditions related thereto.

Accordingly, in a first embodiment, a GPR119 agonists in the context of the present invention is any GPR119 agonists of Formula (I)

Formula I

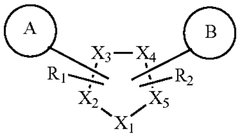

wherein, $X_1$, $X_2$, $X_3$, $X_4$ and $X_5$ are each independently N, O, S or CH; and $X_4$ and $X_5$ may optionally combine to form a five membered ring comprising one or more of heteroatoms each independently selected from N, O and S and the additional five membered ring may be further optionally substituted with one or more of group selected from F, Cl, Br, I, $CF_3$ and $C_{1-6}$ alkyl;

$R_1$ and $R_2$ is independently selected from the group comprising —H, —O, $C_{1-6}$ alkyl, $C_{1-6}$alkoxy, —$(CH_2)$n, amino, —CO, —CONH, —NH(Alkyl), —N$(Alkyl)_2$, —NH-aralkyl, —$CH_2O$, —$OCH(CH_3)_2$, halogen$COOR_3$, —$CONR_3R_4$, $NR_3COR_4$;

$R_3$ and $R_4$ is independently selected from the group comprising hydrogen, or $C_{1-6}$ straight chain or branched chain alkyl which may be further substituted with halogen or $C_{1-6}$ alkyl;

n is 0, 1, 2 or 3.

A is selected from;

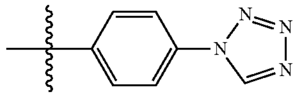

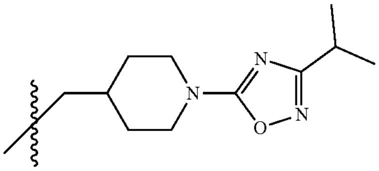

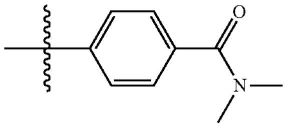

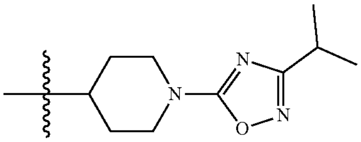

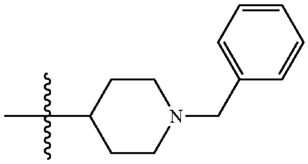

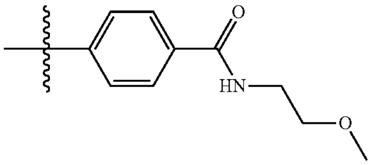

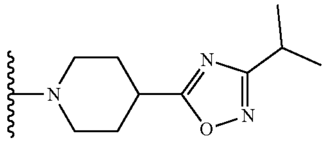

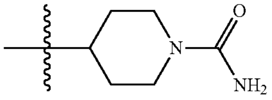

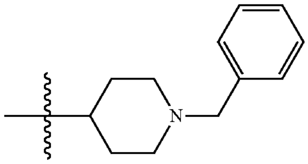

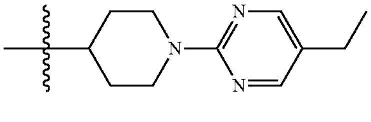

-continued

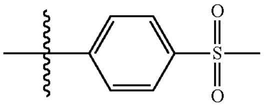

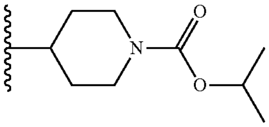

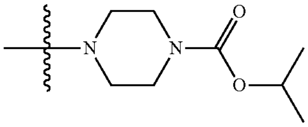

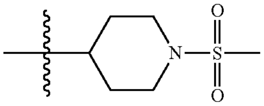

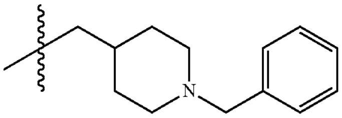

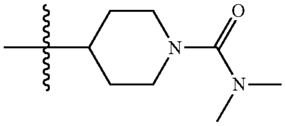

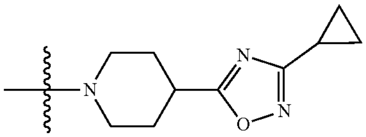

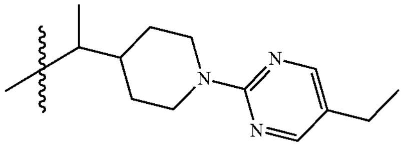

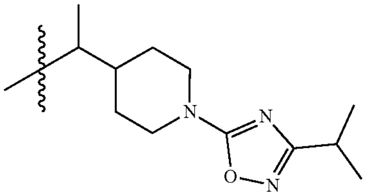

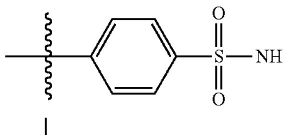

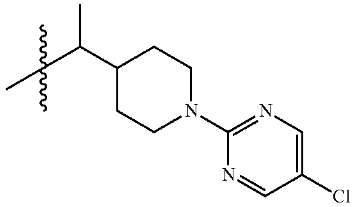

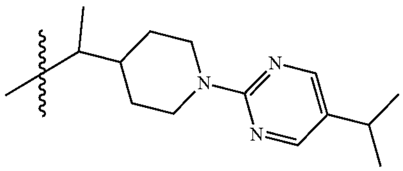

-continued
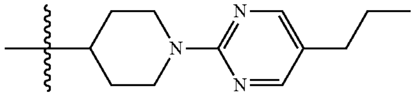
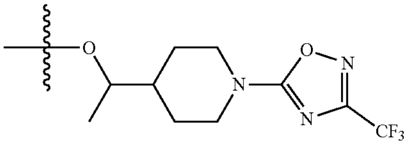
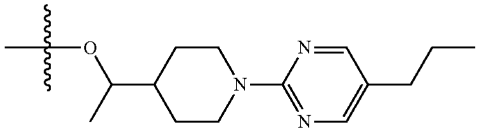
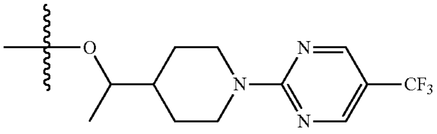
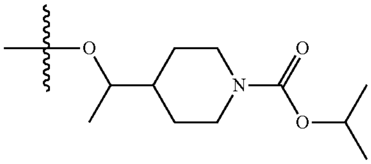
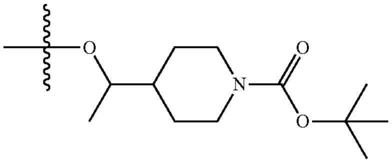
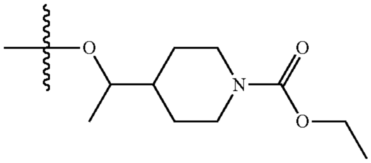
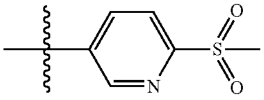
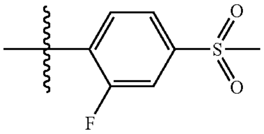
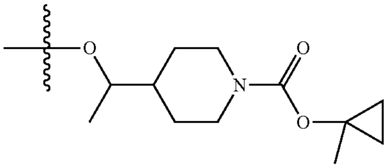
Ring 'B' is be selected from
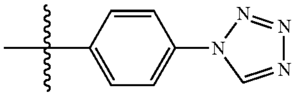
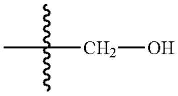
-continued
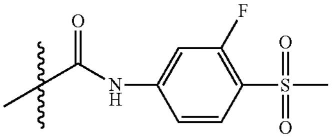
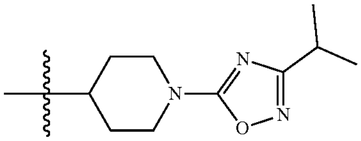
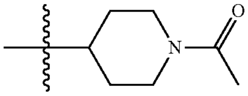
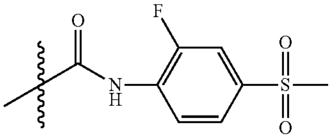
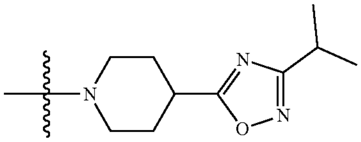
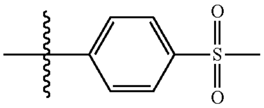
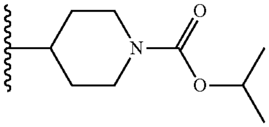
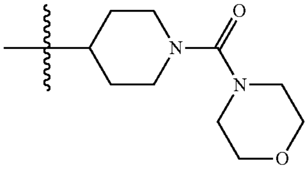
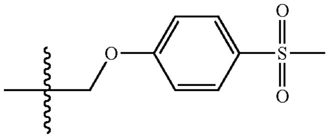
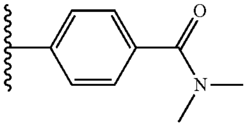
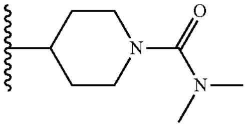
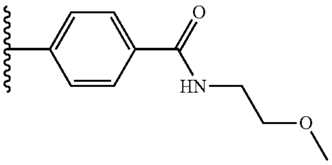
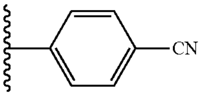
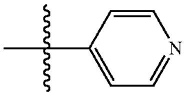

-continued

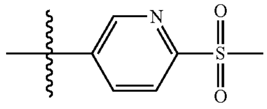
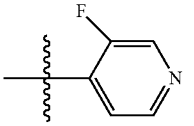
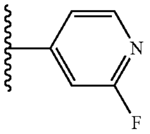
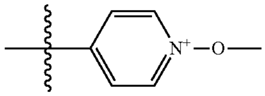
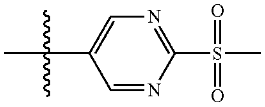
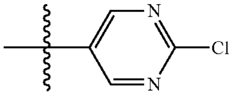
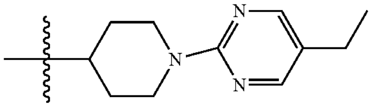
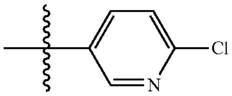
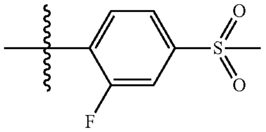
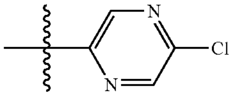
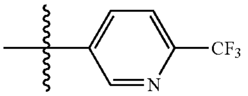
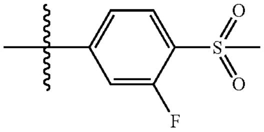
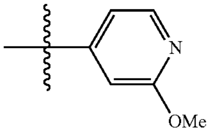
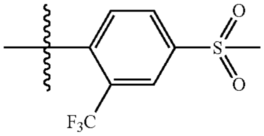
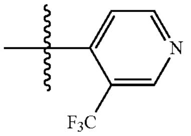
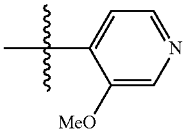
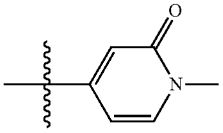
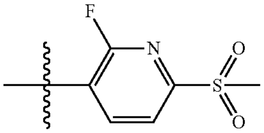
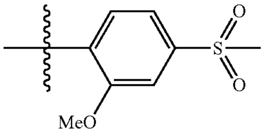
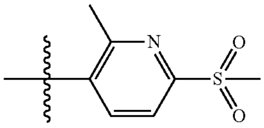
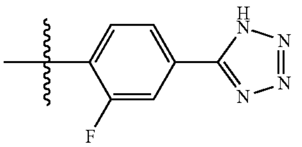
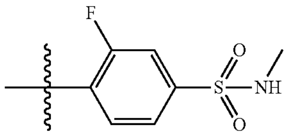
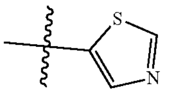
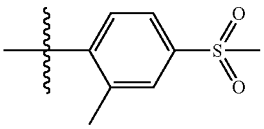

-continued

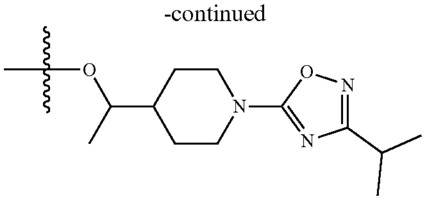

The compound of Formula (I) may involve one or more embodiments. Embodiment of compounds of Formula (I) include compound of Formula (II) as described hereinafter. It is to be understood that the embodiments below are illustrative of the present invention and are not intended to limit the claims to the specific embodiments exemplified. It is also to be understood that the embodiments defined herein may be used independently or in conjunction with any definition and any other embodiment defined herein. Thus the invention contemplates all possible combinations and permutations of the various independently described embodiments. For example, the invention provides compounds of Formula (I) as defined above wherein, $X_4$ and $X_5$ may combine to form a ring comprising one of the heteroatoms each independently selected from N or O.

In other embodiment, specifically provided are compound of Formula (II) of GPR119 agonists, in which, $X_4$ and $X_5$ may combine to form a five membered ring.

Formula II

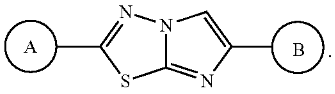

It should be understood that the Formulas (I) and (II) structurally encompasses all geometrical isomers, stereoisomers, and pharmaceutically acceptable salts that may be contemplated from the chemical structure of the genera described herein.

In main embodiment, the present invention provides a pharmaceutical combination comprising GPR119 of Formula I, tautomer, stereoisomer, or pharmaceutically acceptable salt thereof, and at least one DPP-4 inhibitor or its pharmaceutically acceptable salt.

In another embodiment, present invention provides a pharmaceutical combination that includes at least one compound of Formula I, DPP-4 inhibitor and at least one pharmaceutically acceptable excipient.

Accordingly in an embodiment, the present invention provides a pharmaceutical combination comprising:

a) therapeutically effective amount of GPR119 agonist of Formula I;

Formula I

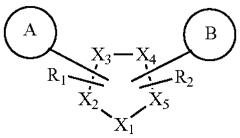

wherein, $X_1$, $X_2$, $X_3$, $X_4$ and $X_5$ are each independently N, O, S or CH; and $X_4$ and $X_5$ may optionally combine to form a five membered ring comprising one or more of heteroatoms each independently selected from N, O and S and the additional five membered ring may be further optionally substituted with one or more of group selected from F, Cl, Br, I, $CF_3$ and $C_{1-6}$ alkyl;

$R_1$ and $R_2$ is independently selected from the group comprising —H, —O, $C_{1-6}$ alkyl, $C_{1-6}$alkoxy, —$(CH_2)$n, amino, —CO, —CONH, —NH(Alkyl), —N$(Alkyl)_2$, —NH-aralkyl, —$CH_2O$, —$OCH(CH_3)_2$, halogen$COOR_3$, —$CONR_3R_4$, $NR_3COR_4$;

$R_3$ and $R_4$ is independently selected from the group comprising hydrogen, or $C_{1-6}$ straight chain or branched chain alkyl which may be further substituted with halogen or $C_{1-6}$ alkyl;

n is 0, 1, 2 or 3.

A is selected from;

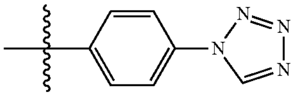

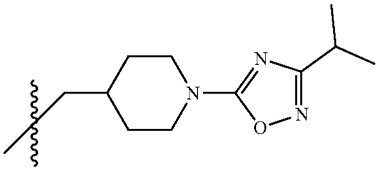

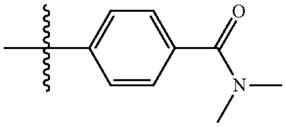

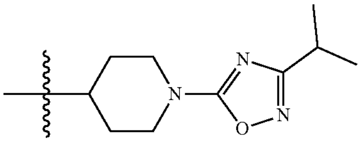

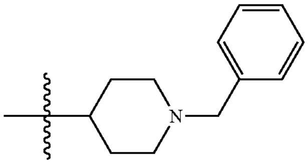

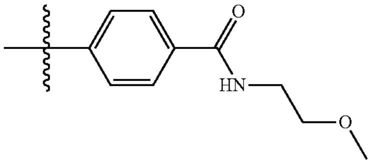

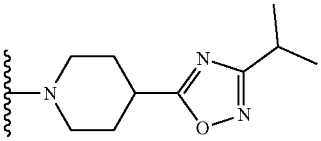

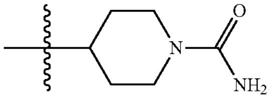

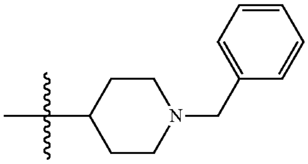

-continued

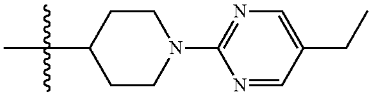

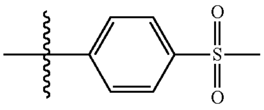

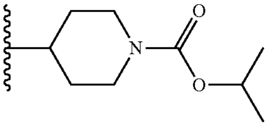

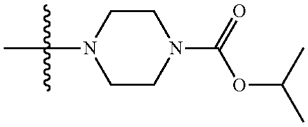

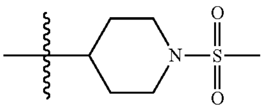

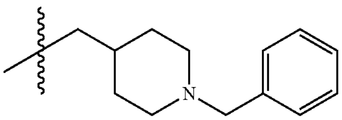

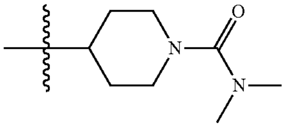

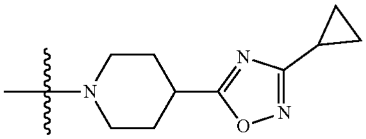

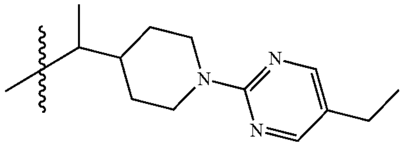

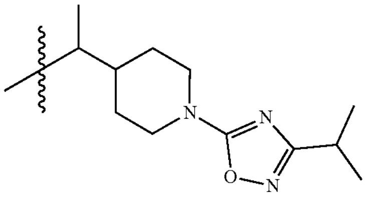

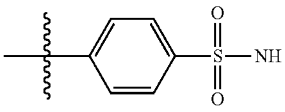

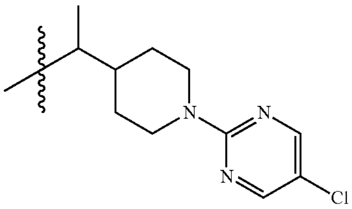

-continued
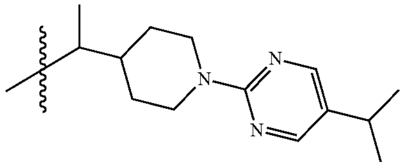
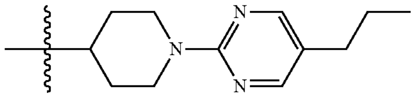
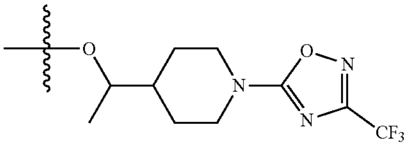
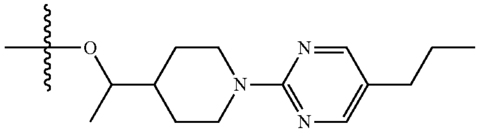
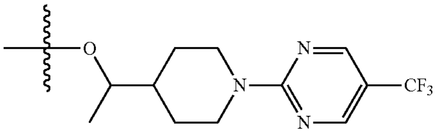
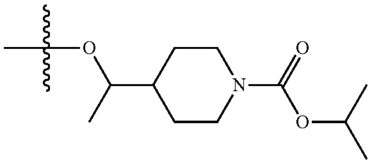
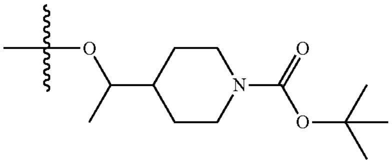
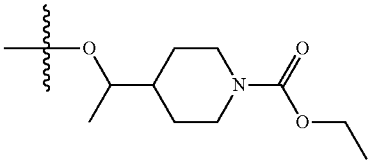
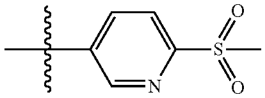
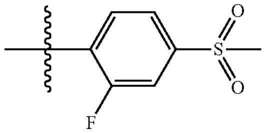
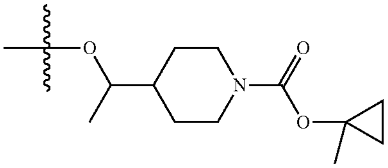
Ring B is be selected from
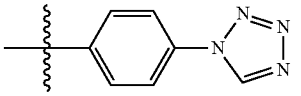
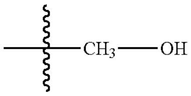
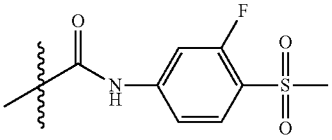
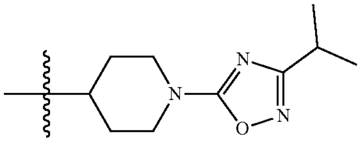
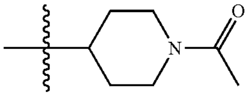
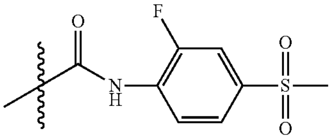
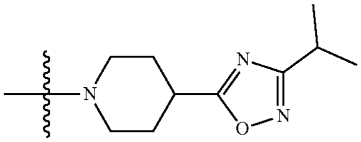
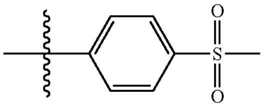
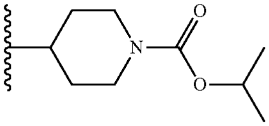
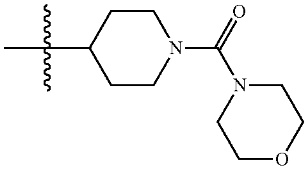
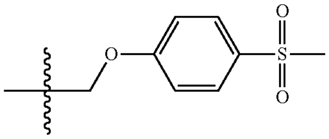
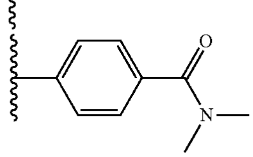
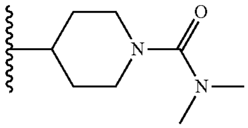
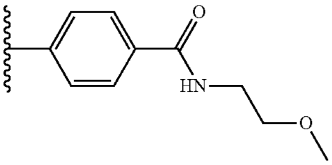

-continued

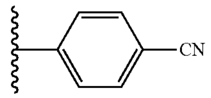
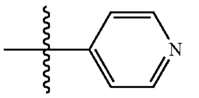
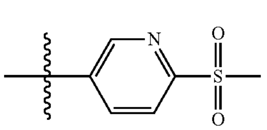
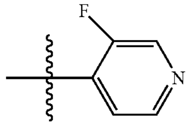
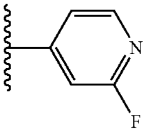
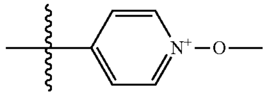
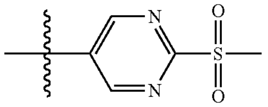
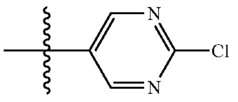
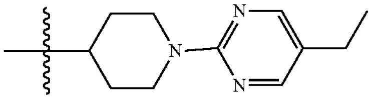
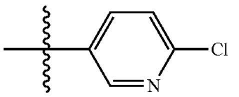
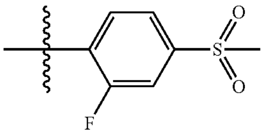
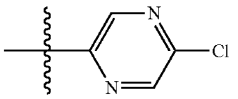
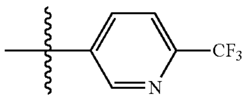
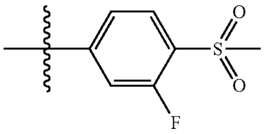
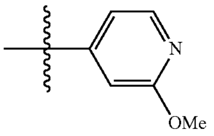
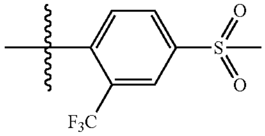
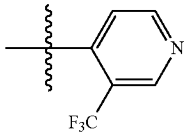
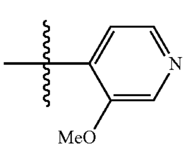
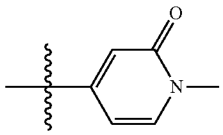
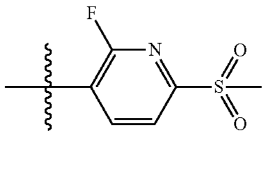
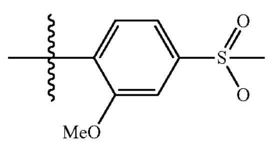
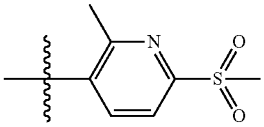
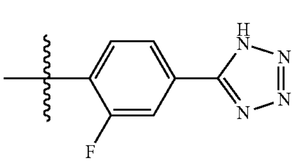
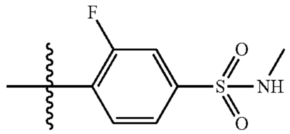
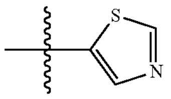

-continued

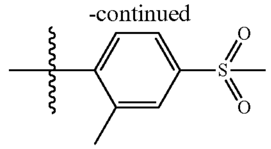
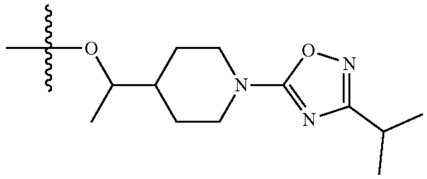

tautomer, stereoisomer, or pharmaceutically acceptable salt thereof;

b) therapeutically effective amount of DPP-4 inhibitor selected from sitagliptin, vildagliptin, saxagliptin, carmegliptin, gosogliptin, alogliptin, linagliptin, melogliptin, gemigliptin, anagliptin, teneligliptin, trelagliptin, dutogliptin, evogliptin, omarigliptin or pharmaceutically acceptable thereof; and c) at least one pharmaceutically acceptable carrier.

As described herein, the pharmaceutical combination of the present invention comprises therapeutic effective amount of GPR119 agonist of Formula I, and DPP-4 inhibitors, wherein said compound of Formula I comprises of:

Formula IA

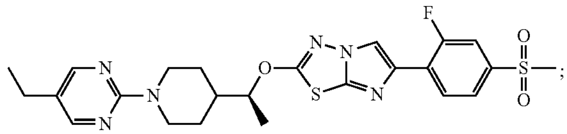
;

Formula IB

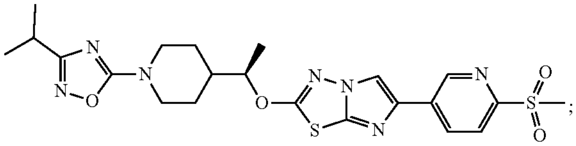
;

Formula IC

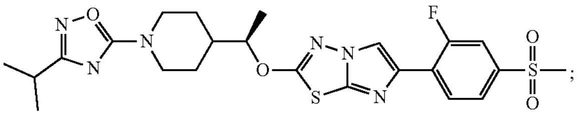
;

Formula ID

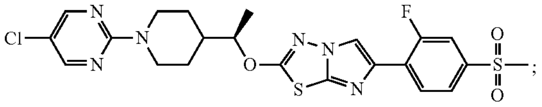
; and

Formula IE

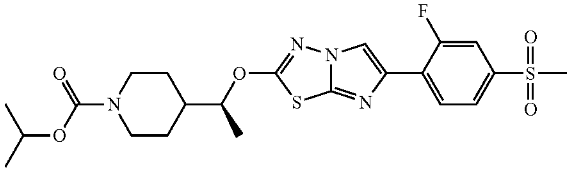

The combination of the present invention may be administered by oral dosage form (including, but not limited to, tablets, granules, fine granules, powders, capsules, caplets, soft capsules, pills, oral solutions, syrups, dry syrups, chewable tablets, troches, effervescent tablets, drops, suspension, fast dissolving tablets, oral fast-dispersing tablets, etc); parenteral dosage form (e.g., intramuscular, intraperitoneal, intravenous, ICV, or infusion, subcutaneous injection, or implant), by inhalation spray, nasal, vaginal, rectal, sublingual, or topical routes of administration and may be formulated, alone or together, in suitable dosage unit formulations i.e. dosage form containing conventional non-toxic pharmaceutically acceptable carriers, adjuvants and vehicles appropriate for each route of administration. The combinations may take such forms as suspensions, solutions, or emulsions in oily or aqueous vehicles, and may contain formulatory agents such as suspending, stabilizing or dispersing agents. Alternatively, the active ingredients may be in powder form, obtained by aseptic isolation of sterile solid or by lyophilisation from solution, for constitution with a suitable vehicle, e.g. sterile, pyrogen-free water, before use.

In another embodiment, the present invention provides a pharmaceutical composition comprising:

a) therapeutically effective amount of GPR119 agonist of Formula I, or isomers, or pharmaceutical acceptable salt thereof;
b) therapeutically effective amount of DPP-4 inhibitor; and
c) at least one pharmaceutically acceptable excipient.

The pharmaceutical combinations according to the invention may contain (GPR119 agonist) and (DPP-4 inhibitor), for example, in a ratio (w/w) (GPR119 agonist):(DPP-4 inhibitor) ranging from 0.001:5000 to 300:1 (w/w), preferably from 1:5 to 200:1, preferably 1:3 to 150:1, more preferably from 1:2 to 100:1.

GPR119 agonist as used in the present invention may be administered in a dose ranging from about 0.001 mg to about 5000 mg, conveniently be presented in a single dose or as divided doses administered at appropriate intervals.

GPR119 agonist as used in the present invention may be administered in a dose ranging from about 0.001 mg to about 1000 mg, conveniently be presented in a single dose or as divided doses administered at appropriate intervals.

DPP-4 (also referred as DPP-IV) inhibitor refers to a class of compounds that inhibit the enzyme dipeptidyl peptidase-4 (DPP-4)/(DPP-IV).

A DPP-4 inhibitor can be any compound which inhibits the DPP-4 enzyme. DPP-4 inhibitor can be selected from the group consisting of, but not limited to, sitagliptin, vildagliptin, saxagliptin, carmegliptin, gosogliptin, alogliptin, linagliptin, melogliptin, gemigliptin, anagliptin, teneligliptin, trelagliptin, dutogliptin, evogliptin, omarigliptin or a pharmaceutically acceptable salt thereof.

DPP-4 inhibitor as used in the present invention may be administered in a dose ranging from about 1 mg to about 500 mg.

Sitagliptin (MK-0431) refers to (3R)-3-amino-1-[3-(trifluoromethyl)-5,6,7,8-tetrahydro-5H-[1,2,4]triazolo-[4,3-a]pyrazin-7-yl]-4-(2,4,5-trifluorophenyl) butan-1-one, also named (2R)-4-oxo-4-[3-(trifluoromethyl)-5,6-dihydro[1,2,4]triazolo[4,3-a]pyrazin-7(8H)-yl]-1-(2,4,5-trifluorophenyl) butan-2-amine. In one embodiment, sitagliptin is in the form of its dihydrogenphosphate salt, i.e. sitagliptin phosphate. In a further embodiment, sitagliptin phosphate is in the form of a crystalline anhydrate or monohydrate. In a preferred embodiment, sitagliptin phosphate monohydrate. Sitagliptin can be administered in dose range of 1-300 mg. An oral dosage strength of the DPP-4 inhibitor sitagliptin is usually between 25 and 200 mg of the active moiety.

Linagliptin (BI 1356) refers to 1-[(4-methyl-quinazolin-2-yl)methyl]-3-methyl-7-(2-butyn-1-yl)-8-(3-(R)-amino-piperidin-1-yl)-xanthine or a pharmaceutically acceptable salt thereof. The dosage typically required of linagliptin when administered orally is 0.5 mg to 10 mg per patient per day.

Vildagliptin (LAF-237) refers to (2S)-{[(3-hydroxyadamantan-1-yl)amino]acetyl}pyrrolidine-2-carbonitrile, also named(S)-1-[(3-hydroxy-1-adamantyl)amino]acetyl-2-cyano-pyrrolidine. An oral dosage range of the DPP-4 inhibitor vildagliptin is usually between 10 and 150 mg daily.

Saxagliptin (BMS-477118) refers to (1S,3S,5S)-2-{(2S)-2-amino-2-(3-hydroxyadamantan-1-yl)acetyl}-2-azabicyclo[3.1.0]hexane-3-carbonitrile, also named (S)-3-hydroxyadamantylglycine-L-cis-4,5-methanoprolinenitrile or a pharmaceutically acceptable salt thereof. Saxagliptin may be administered to a patient at an oral daily dose of between 2.5 mg/day and 100 mg/day, optionally between 2.5 mg and 50 mg.

Alogliptin (SYR-322) refers to 2-({6-[(3R)-3-aminopiperidin-1-yl]-3-methyl-2,4-dioxo-3,4-dihydro-2H-p-yrimidin-1-yl}methyl)benzonitrile or a pharmaceutically acceptable salt thereof. Alogliptin may be administered to a patient at an oral daily dose of between 5 mg/day and 250 mg/day.

Teneligliptin refers to 3-{(2S,4S)-4-[4-(3-Methyl-1-phenyl-1H-pyrazol-5-yl)piperazin-1-yl]pyrroli-din-2-ylcarbonyl}thiazolidine or a pharmaceutically acceptable salt thereof. In adults, teneligliptin is orally administered at a dosage of 20 mg once daily, which can be increased up to 40 mg per day. Because the metabolites of this drug are eliminated via renal and hepatic excretion, no dose adjustment is necessary in patients with renal impairment.

The combination as mentioned herein comprises GPR119 agonist and DPP-4 inhibitor wherein said GPR119 agonist and DPP-4 inhibitor may be taken as their pharmaceutically acceptable salts and/or hydrates, solvates, and polymorphic forms thereof. All stereoisomers of the present compounds, such as those which may exist due to asymmetric carbons, including enantiomeric and diastereomeric forms, are contemplated within the scope of this invention. The compounds of the present invention may be present in their enantiomeric pure forms or their racemic mixtures. Further, the compounds in the present invention can be in form of solid form.

The combinations or combined uses as per the present invention envisage simultaneous, sequential, alternate or separate administration of the two active components.

The pharmaceutical combination as per the present invention can be given in a single dose or as divided doses administered at appropriate intervals, e.g. as two, three, four or more sub-doses per patient per day, with or without food.

The present invention further provides a pharmaceutical combination comprising GPR119 agonist, DPP-4 inhibitor and optionally one or more pharmaceutically acceptable excipients. Each the drugs can be administered in a single dosage form or each in separate dosage forms, or they can be administered by different routes.

As discussed above this invention provides GPR119 agonists that in combination with DPP-4 inhibitors have biological properties useful for the treatment or prevention of cardiovascular and metabolic disorders. In certain embodiment, the present invention provides a combination therapeutic product or a pharmaceutical combination comprising a DPP-4 inhibitor as defined herein and a GPR119 agonist as defined herein, for simultaneous or sequential use in the treatment or prevention of cardiovascular and metabolic disorders, including type 2 diabetes mellitus, non-alcoholic fatty liver disease (NAFLD), NAFL, NASH, dyslipidemia, and conditions related thereto.

Accordingly, in an embodiment, the present invention provides a method of treating Type 2 diabetes comprising administering, (a) therapeutically effective amount of GPR119 agonist of Formula I, Formula I

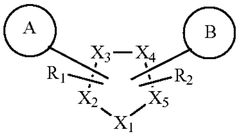

wherein, $X_1$, $X_2$, $X_3$, $X_4$ and $X_5$ are each independently N, O, S or CH; and $X_4$ and $X_5$ may optionally combine to form a five membered ring comprising one or more of heteroatoms each independently selected from N, O and S and the additional five membered ring may be further optionally substituted with one or more of group selected from F, Cl, Br, I, $CF_3$ and $C_{1-6}$ alkyl;

$R_1$ and $R_2$ is independently selected from the group comprising —H, —O, $C_{1-6}$ alkyl, $C_{1-6}$alkoxy, —$(CH_2)$n, amino, —CO, —CONH, —NH(Alkyl), —N$(Alkyl)_2$, —NH-aralkyl, —$CH_2O$, —$OCH(CH_3)_2$, halogen$COOR_3$, —$CONR_3R_4$, $NR_3COR_4$;

$R_3$ and $R_4$ is independently selected from the group comprising hydrogen, or $C_{1-6}$ straight chain or branched chain alkyl which may be further substituted with halogen or $C_{1-6}$ alkyl;

n is 0, 1, 2 or 3.

A is selected from;

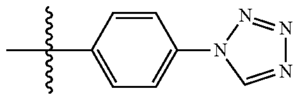

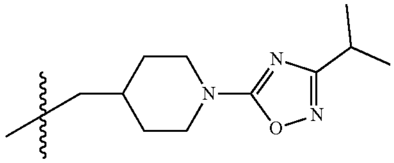

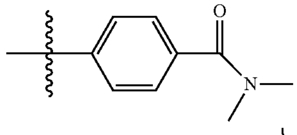

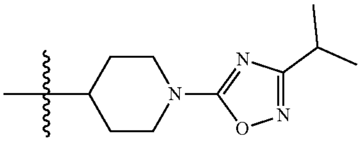

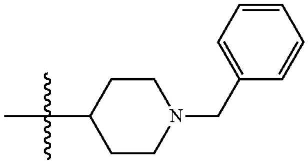

-continued

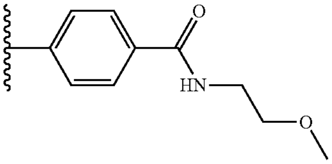

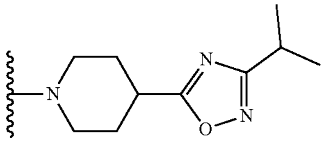

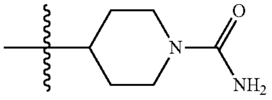

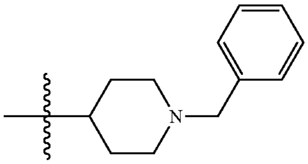

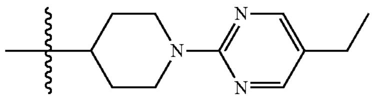

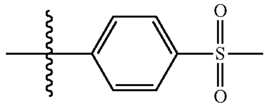

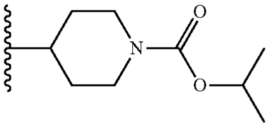

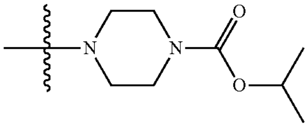

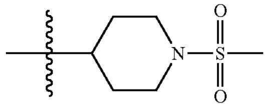

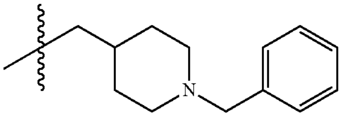

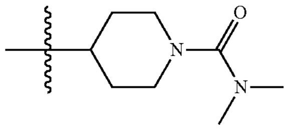

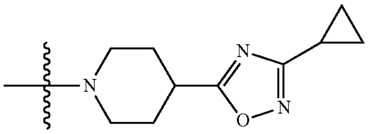

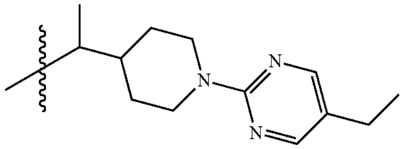

-continued
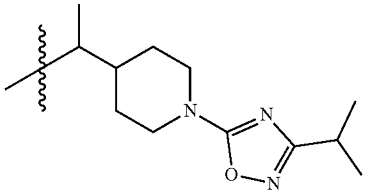
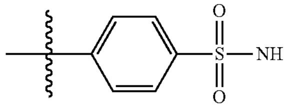
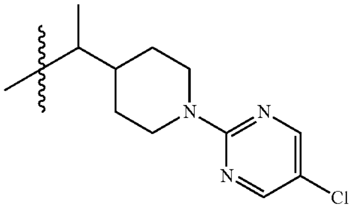
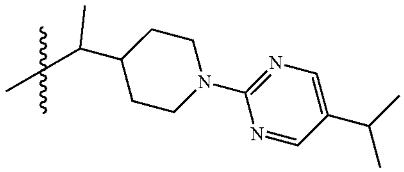
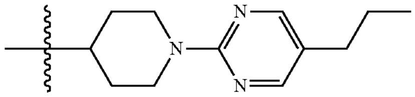
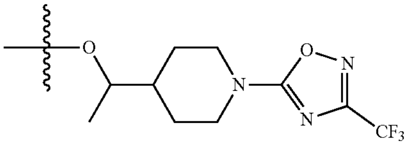
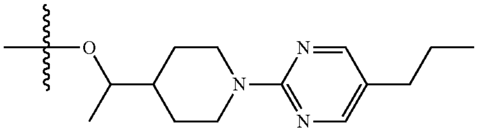
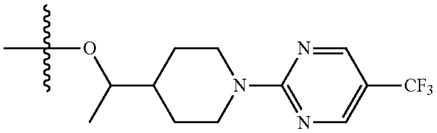
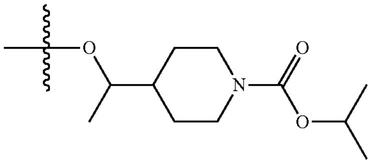
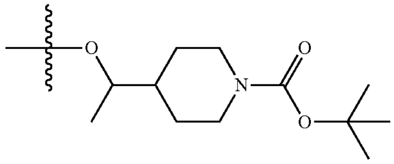
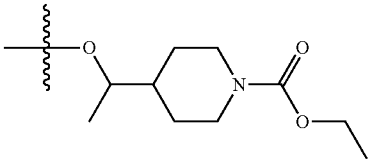
-continued
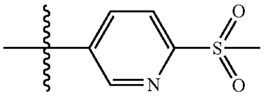
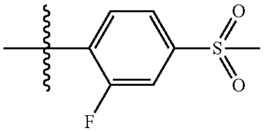
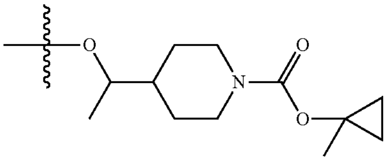
Ring B is be selected from
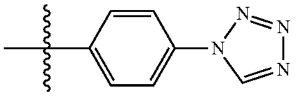
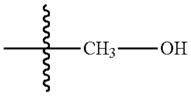
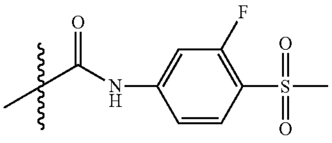
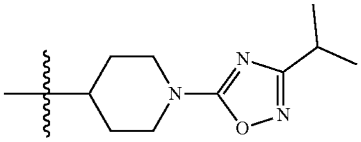
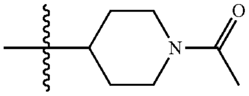
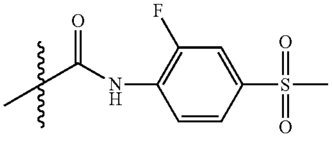
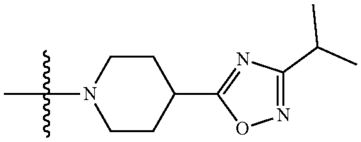
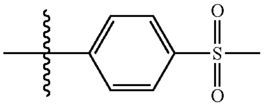
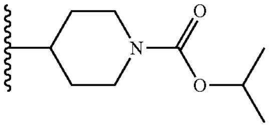
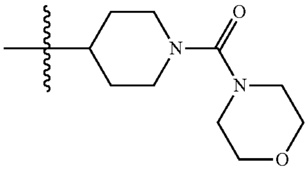

-continued

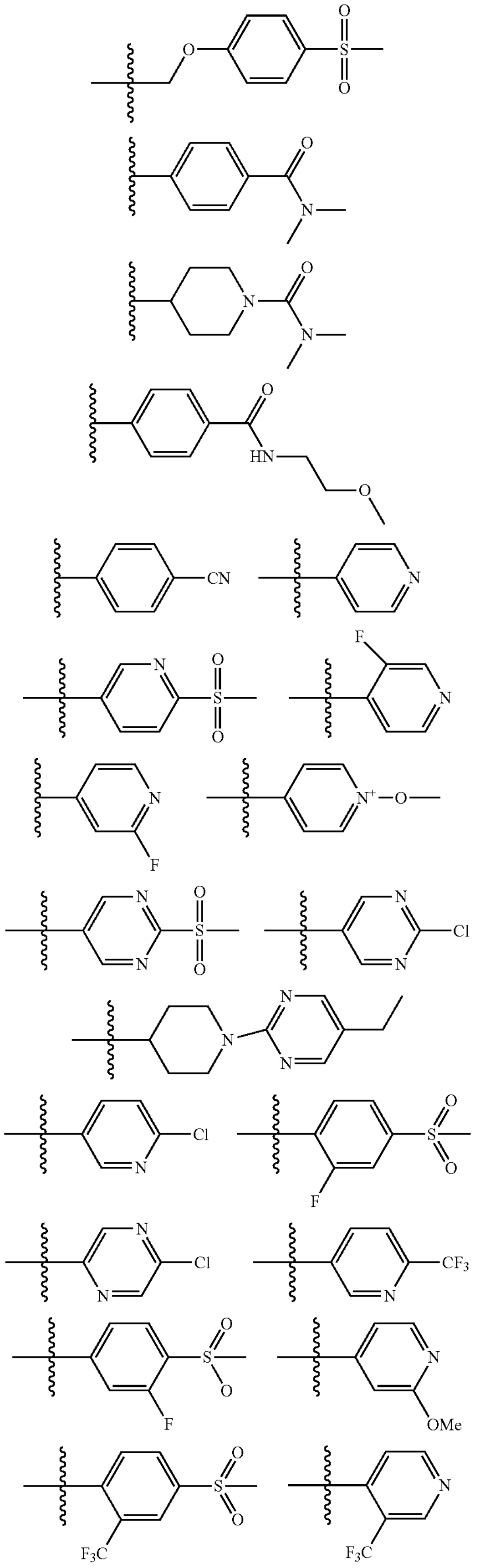

-continued

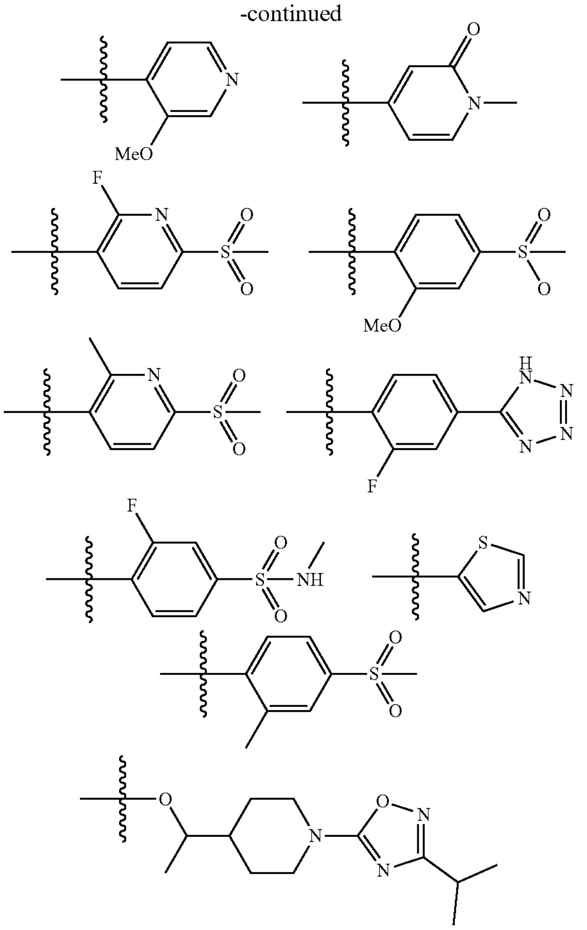

tautomer, stereoisomer, or pharmaceutically acceptable salt thereof;

b) therapeutically effective amount of DPP-4 inhibitor or its pharmaceutically acceptable salt; and c) at least one pharmaceutically acceptable carrier.

The combinations according to the present invention may be useful in one or more of the following methods for preventing, slowing progression of, delaying, or treating a metabolic disorders; for improving glycemic control and/or for reducing of fasting plasma glucose, of postprandial plasma glucose and/or of glycosylated hemoglobin HbA1c; for preventing, slowing, delaying or reversing progression from impaired glucose tolerance, insulin resistance and/or from metabolic syndrome to type 2 diabetes mellitus; for preventing, slowing progression of, delaying or treating of a condition or disorder selected from the group consisting of complications of diabetes mellitus; for reducing the weight or preventing an increase of the weight or facilitating a reduction of the weight; for preventing or treating the degeneration of pancreatic beta cells and/or for improving and/or restoring the functionality of pancreatic beta cells and/or restoring the functionality of pancreatic insulin secretion; and/or for maintaining and/or improving the insulin sensitivity and/or for treating or preventing hyperinsulinemia and/or insulin resistance.

Accordingly, examples of such diseases or disorders amenable to the therapy of this invention include, without being restricted to, Type 1 diabetes, Type 2 diabetes, inadequate glucose tolerance, insulin resistance, hyperglycemia.

Various other conditions which may be associated with the metabolic disorders, such as, increased abdominal girth, obesity, hypertension, liver disorders (e.g. fatty liver, non-alcoholic fatty liver disease (NAFLD), nonalcoholic steato-hepatitis (NASH), steatosis, cirrhosis), dyslipidemia (e.g. hypertriglyceridemia, hyperlipidemia, hypercholesterolemia, hyperlipoproteinemia and/or low HDL), hypercoagulability, hyperuricemia, thromboses, hypercoagulable and prothrombotic states (arterial and venous), and endothelial dysfunction; Cardiovascular diseases, e.g. Chronic heart failure, myocardial infarction, hypertensive heart disease, cardiomyopathy and stroke; Micro and macrovascular disorders, such as retinopathy, atherosclerosis, nephropathy, microalbuminuria, chronic systemic inflammation and neuropathy; Bone-related diseases and disorders characterized by reduced bone mass, such as, osteoporosis, rheumatoid arthritis and osteoarthritis.

In certain embodiment, the combinations of this invention may be useful for anti-diabetic therapy or prophylaxis in diabetic (especially obese) patients suffering from severe or highly insulin resistance.

In a preferred embodiment, the present invention provides a pharmaceutical combination comprising GPR119 agonist, DPP-4 inhibitor and optionally one or more pharmaceutically acceptable excipients, wherein said combination shows synergistic effect towards the treatment or prevention of the cardiovascular and metabolic disorders, including diabetes mellitus, non-alcoholic fatty liver disease (NAFLD), NAFL, NASH, dyslipidemia, and related disorders thereto.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions/combinations of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

In certain embodiment, the pharmaceutical combination of the present invention which is present as a separate or multiple dosage form, preferably as a kit, is useful in combination therapy to flexibly suit the individual therapeutic needs of the patient.

In another embodiment, the present invention provides a kit comprising, (a) first component containing a dosage form comprising GPR119 agonist of Formula I a tautomer, stereoisomer, or pharmaceutically acceptable salt thereof;

(b) second component containing a dosage form comprising DPP-4 inhibitor or pharmaceutically acceptable salt thereof; and (c) optionally one or more pharmaceutically acceptable carrier.

GPR119, a G-protein coupled receptor, which is expressed predominantly in pancreatic β cells and intestinal enteroendocrine L cells. GPR119 agonists acts via dual mechanism of action 1) activation of GPR119 receptor in pancreatic β cells results in direct stimulation of glucose-dependent insulin secretion 2) activation of GPR119 in entero-endocrine cells results in stimulation of incretin release (GLP-1 & GIP), leading to improved acute glucose tolerance. Hence, activation of GPR119 receptor by ligands is thought to be a feasible strategy for the treatment of type 2 diabetes. Several small molecule GPR119 agonists are developed and studied for efficacy in preclinical models and few are in clinical investigation for type 2 diabetes.

EXAMPLES

Example 1: Oral Glucose Tolerance Test (OGTT Study)

Experiment

OGTT study is conducted in male Sprague dawley rats. Animals of 8-10 weeks old were kept for overnight fasting (only water was provided ad libitum). Eight male rats were randomized based on basal glucose values into four different groups. Vehicle (0.5% Tween 80 and 99.5% NaCMC in water (0.5% w/v) was administered to control animals and remaining groups were administered with test compound prepared in vehicle at respective doses orally. Blood samples were collected immediately after test compound administration (which was −30 min time point). Blood glucose was monitored post 30 min of dose administration (which was a zero min time point). All animals received 2 g/kg/10 ml (20%) of Glucose solution orally. After glucose administration, glucose levels were estimated at different time points (5, 15, 30, 60 & 120 min). Estimation of blood glucose level was done by strip method. (Accu-Check active blood glucometer). Blood glucose AUC was calculated from the samples collected at respective time points. The data are presented as mean±SEM. One-way ANOVA followed by Tukey's multiple comparison test was performed to understand the statistical significance of the parameters studied.

Result

GPR119 agonist of Formula IA (10 mg/kg), showed a glucose reduction of 16% compared to vehicle and sitagliptin, 3 mg/kg, showed a glucose reduction of 15% compared to vehicle. The combination of Compound of Formula IA (10 mg/kg/wt) plus sitagliptin (3 mg/kg/wt) showed 25% reduction in glucose compared to vehicle control. The glucose reduction observed in the combination group was statistically significant compared to monotherapy as represented in FIG. 1

The results of this study demonstrated that the combination of GPR119 agonist of Formula I of the present invention, and DPP-4 inhibitor showed glucose reduction in an unexpected and highly synergistic fashion.

Example 2: GLP-1 Estimation

GLP-1 estimation is conducted in male Sprague dawley rats. Animals of 8-10 weeks old were kept for overnight fasting (only water was provided ad libitum). Eight male rats were randomized based on basal glucose values into four different groups. Vehicle (0.5% Tween 80 and 99.5% NaCMC in water (0.5% w/v) was administered to control animals and remaining groups were administered with test compound prepared in vehicle at respective doses orally.

For active GLP-1 estimation, blood was collected by retro orbital puncture under isoflurane anesthesia. Active GLP-1 levels were estimated from the collected plasma at −30, 0, 5, 15, 30 & 60 min time points. Blood collection (Approximately 400-500 μl) was done by retro orbital puncture under isoflurane anesthesia with the help of DPP-4 inhibitor (#DPP4-010, Merck-Millipore) rinsed capillaries and collected into pre-coated Eppendorf (10 μl/ml of blood) with DPP-4 inhibitor.

Result

Figure 2:
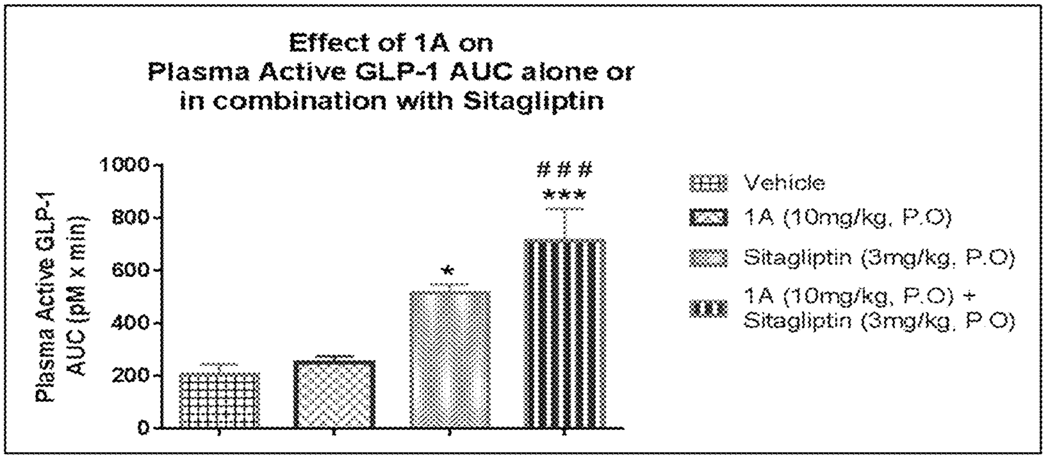
FIG. 2. Effect of GPR119 agonist Formula 1A on active GLP-1 levels in male Sprague Dawley rats. Formula 1A was administered to the rats and GLP-1 levels were estimated at different time points (0, 5, 15, 30 & 60 min) and compared to vehicle group. Data was analysed by One-Way ANOVA followed by Dunnett's Multiple Comparison Test. *P<0.05, P<0.01, *P<0.001 vs vehicle control. Vehicle used was 0.5% Tween 80 and 99.5% NaCMC in water (0.5% w/v).

GPR119 agonist of Formula IA, 10 mg/kg/wt, showed an increase in active GLP-1 secretion by 123% compared to vehicle and sitagliptin, 3 mg/kg/wt, showed an increase in active GLP-1 secretion by 253% compared to vehicle. The combination of compound of Formula IA (10 mg/kg/wt) plus sitagliptin, (3 mg/kg/wt), showed 350% increase in active GLP-1 secretion compared to vehicle control. The active GLP-1 secretion observed in the combination group was statistically significant compared to monotherapy as represented in FIG. 2.

The results as shown above demonstrated a powerful synergistic effect for the combination of GPR119 agonist of Formula I of the present invention, and DPP-4 inhibitor on the GLP-1 secretion, wherein the GLP-1 secretion is drastically increased.

Example 3

Tablet Containing 600 mg of Active Substance (i.e. combination of GPR119 agonist of Formula I (500 mg) and sitagliptin phosphate (100 mg))

Composition:

(1) Active substance 600.0 mg
(2) Lactose 98.0 mg
(3) Maize starch 50.0 mg
(4) Magnesium stearate 2.0 mg Preparation:

Active substance, lactose and maize starch are mixed together and granulated. Magnesium stearate is added to the granules. The granules were then compressed into tablets.

Example 4

Tablet Containing 550 mg of Active Substance (i.e. combination of GPR119 agonist of Formula I (500 mg) and sitagliptin phosphate (50 mg))

Composition:

(1) Active substance 550.0 mg
(2) Lactose 98.0 mg
(3) Maize starch 50.0 mg
(4) Magnesium stearate 2.0 mg Preparation:

Active substance, lactose and maize starch are mixed together and granulated. Magnesium stearate is added to the granules. The granules were then compressed into tablets.

Example 5

Tablet Containing 500 mg of Active Substance (combination of GPR119 agonist of Formula I (495 mg) and linagliptin (5 mg))

Composition:

(1) Active substance 500.0 mg
(2) Lactose 136.0 mg
(3) Maize starch 80.0 mg
(4) Magnesium stearate 2.0 mg Preparation:

Active substance, lactose and maize starch are mixed together and granulated. Magnesium stearate is added to the granules. The granules were then compressed into tablets.

Example 6

Tablet Containing 550 mg of Active Substance (i.e. combination of GPR119 agonist of Formula I (500 mg) and vildagliptin (50 mg))

Composition:

(1) Active substance 550.0 mg
(2) Dried maize starch 58.0 mg
(4) Magnesium stearate 2.0 mg Preparation:

Active substance, lactose and maize starch are mixed together and granulated. Magnesium stearate is added to the granules. The granules were then compressed into tablets.

The invention claimed is:

1. A pharmaceutical combination comprising:

(a) a GPR119 agonist of Formula IA:

Formula IA

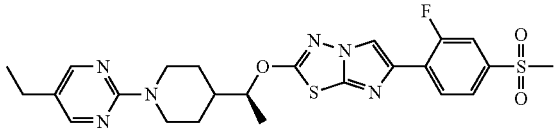

, tautomers thereof, stereoisomers thereof, and pharmaceutically acceptable salts thereof in a range from 0.001 mg to 1000 mg; and (b) sitagliptin or a pharmaceutically acceptable salt thereof in a range from 25 mg to 200 mg.

2. The pharmaceutical combination as claimed in claim 1, wherein the combination further comprises at least one pharmaceutically acceptable carrier.

3. The pharmaceutical combination as claimed in claim 1, wherein the GPR119 agonist and sitagliptin are present in a single dosage form.

4. The pharmaceutical combination as claimed in claim 1, wherein the GPR119 agonist and sitagliptin are present each in a separate dosage form.

5. The pharmaceutical combination as claimed in claim 1, wherein the GPR119 agonist and sitagliptin are administered simultaneously, sequentially or alternately.

6. The pharmaceutical combination as claimed in claim 1, wherein the pharmaceutical combination is in an oral dosage form.

7. A kit comprising:

(a) a first component comprising a GPR119 agonist of Formula IA:

Formula IA

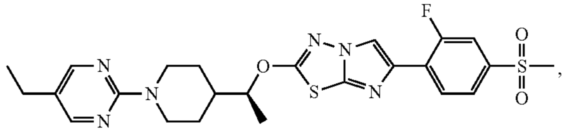

, tautomers thereof, stereoisomers thereof, and pharmaceutically acceptable salts thereof in a range from 0.001 mg to 1000 mg;

(b) a second component comprising sitagliptin or a pharmaceutically acceptable salt thereof in a range from 25 mg to 200 mg, and (c) optionally one or more pharmaceutically acceptable carriers.

* * * * *